United States Patent [19]

Negrutiu et al.

[11] Patent Number: 5,508,184
[45] Date of Patent: Apr. 16, 1996

[54] PROCESS FOR TRANSFORMING PLANT PROTOPLAST

[75] Inventors: Ioan Negrutiu, Bruxelles, Belgium; Ingo Potrykus, Magden, Switzerland

[73] Assignee: Ciba-Geigy Corporation, Tarrytown, N.Y.

[21] Appl. No.: 488,517

[22] Filed: Feb. 27, 1990

Related U.S. Application Data

[63] Continuation of Ser. No. 128,014, Dec. 2, 1987, abandoned.

[30] Foreign Application Priority Data

Dec. 5, 1986 [CH] Switzerland .......... 4866/86-8 4866/86

[51] Int. Cl.$^6$ ..................... C12N 15/00; C12N 15/05; C12N 15/09
[52] U.S. Cl. ..................... 435/172.3; 435/172.1; 435/240.4; 435/240.47; 435/240.49; 935/52; 935/56; 800/205
[58] Field of Search ................ 435/172.3, 240, 435/240.47, 172.2; 935/56, 52

[56] References Cited

U.S. PATENT DOCUMENTS 4,684,611  8/1987  Schilperoort et al. ............ 435/172.3

FOREIGN PATENT DOCUMENTS 0193259  9/1986  European Pat. Off. ........ C12N 15/00
2140822A  12/1984  United Kingdom .
2159173A  11/1985  United Kingdom .

OTHER PUBLICATIONS

J. Paszkowski et al., Embo J. 3, 2717 (1984).
H. Lörz et al., Mol. Gen. Genet. 199, 178 (1985).
I. Potrykus et al, Molec. Gen. Genet. Rep. 3, 199, (1985) p. 183.
I. Potrykus e tal., Plant Molec. Biol. Rep. 3, 117 (1985).
R. D. Shillito et al, Bio/Gechnology 3, 1099 (1985).
M. Fromm et al., Proc. Natl. Acad. Sci. U.S.A. 82, 5824 (1985).
Plant Molecular Biology, 8, pp. 363–373 (1987) I. Negrutiu et al.
Shillito et al., *Biotechnology*, 3:1099–1103 (1985).
Negrutiu et al., in Mulcahy et al. (Ed.), *Biotechnology and Ecology of Cotton* (1985).
Gamberg O. L., (1984) "Plant Cell Cultures. Nutution & Media" An: Cell Culture & Samatre Cell Genetecs of Plants. Oo/1. Laboratory Procedures and their Applcation. Editor I. K. Ooset. Academic Press, pp. 20–21.
Krens et al (1982) Nature vol. 296, pp. 72–74.
Waldron et al. (1985) PL. Mol. Bio. Reporter vol. 3 #4 pp. 169–173.
Klebe et al. (1983) Gene, 25 pp. 333–341.
Barton et al. (1987) Plant Physiology pp. 1103–1109.
Goodman et al. (1987) Science 236, pp. 48–54.
Keith et al. (1986) The EMBO J. vol. 5 No. 10 pp. 2419–2425.
Damm et al., Mol. Gen. Genet, 217, pp. 6–12 (1989).
Datta et al., Bio/Technology, vol. 8, pp. 736–740 (1990).
Kohler et al., Plant Molecular Biology, vol. 12, pp. 189–199 (1989).

(List continued on next page.)

*Primary Examiner*—Gary Benzion
*Attorney, Agent, or Firm*—James Scott Elmer

[57] ABSTRACT

The present invention relates to an improved process for transforming plant protoplasts using simple, purely chemical, process steps, and to the plant material obtainable by this method.

The transfer of the genetic material into the plant cell is carried out directly, without the use of a natural plant-infective system such as a plant bacterium or plant virus, and without transfer by insects or phytopathogenic fungi, by joint incubation in a suitable incubation medium of the DNA to be transformed and plant protoplasts.

In this manner, desired genes can very simply and efficiently be transferred to plant material, resulting in plants with improved properties.

34 Claims, 2 Drawing Sheets

OTHER PUBLICATIONS

Moyne et al., Plant Cell Reports, vol. 8, pp. 97–100 (1989).
Cellular and Molecular Biology, Editor in Chief: Frederick C. Newhardt, 1, pp. 7–15 (1982).
Immunology of the Bacterial Cell Envelope, Editors: D. E. s. Stewart–Tull, et al., pp. 355–359 and 383 (1985).
In Synopsis and Classification of Living Organisms, McGraw–Hill, Inc., vol. 2, pp. 1065–1066 (1982).

Fig. 2 a)
b)

a) 15 mM MgCl$_2$
b) 30 mM MgCl$_2$

PROCESS FOR TRANSFORMING PLANT PROTOPLAST

This application is a continuation of application Ser. No. 128,014, filed Dec. 2, 1987, now abandoned.

The present invention relates to an improved process for transforming plant protoplasts using simple, purely chemical, process steps, and to the plant material obtainable by this process.

It is possible by introducing new genetic information into plant material to produce plants with new and/or improved properties. In view of the rapid increase in world population and the associated greater need for foodstuffs and raw materials, increasing the yield of useful plants and also increased extraction of plant contents, especially progress in the field of foodstuffs and medicines, are amongst the most urgent tasks of biological research. In this connection, for example the following should be mentioned as essential aspects: increasing the resistance of useful plants to unfavourable soil conditions or climatic conditions, to diseases and pests, increasing resistance to plant-protecting agents such as insecticides, herbicides, fungicides and bactericides, and beneficially modifying the nutrient content or the yield of plants. Such desirable effects could in general be brought about by induction or increased formation of protective substances, valuable proteins or toxins. Influencing the plant genotype appropriately can be effected, for example, by introducing a foreign gene into the plant cells in a controlled manner without using conventional plant-breeding techniques.

The following definitions apply for the present invention:

plant material: parts of plant viable as such or in culture, such as protoplasts, cells, calluses, tissue, embryos, plant organs, buds, seeds, inter alia and also whole plants structural gene with flanking expression gene: signals structural gene: protein-coding DNA sequence expression signals: promoter signal and termination signal plant-active expression signal: expression signal that is capable of functioning in plants.

promoter signal: signal initiating transcription termination signal: signal terminating transcription enhancer signal: signal enhancing transcription replication signal: signal rendering possible DNA replication integration signal: DNA sequence that promotes the integration of the gene into the genomic DNA hybrid gene: gene constructed from heterologous DNA sequences, that is to say, DNA sequences of different origin, it being possible for the DNA sequences to be natural DNA sequences, c-DNA sequences or synthetic DNA sequences.

supporting DNA: neutral DNA sequence flanking the gene, that is to say a DNA sequence not participating in the function of the gene carrier DNA: neutral DNA without transforming gene, which is admixed with the transforming gene in order to protect it against nucleases isolated gene: DNA sequence separated from the original DNA and coding for a single protein NPT-II-gene: neomycin-3'-phosphotransferase gene, type II of transposon Tn 5 [[1] Rothstein, S. J. and W. S. Reznikoff, Cell 2-3, 191–199, (1981)]

genomic DNA: DNA of a plant genome (all or a portion thereof)

c-DNA: copy of an m-RNA produced by reverse transcriptase.

The transfer of DNA sequences into plant cells using genetically manipulated plant bacteria is known from publications in the literature of the art such as, for example, [2] Nature, vol. 303, 209–213 (1983); [3] Nature, vol. 304, 184–187 (1983); [4] Scientific American 248(6), 50–59 (1983); [5] EMBO Journal 2(6), 987–995 (1983); [6] Science 222,476–482 (1983); [7] Science 223, 496–498 (1984); or [8] Proc. Natl. Acad. Sci. USA 80, 4803–4807 (1983). In the processes described therein, the natural plant-infective properties of these bacteria are exploited to insert new genetic material into plant cells. Hitherto, plant pathogens in particular, such as, for example, Agrobacterium tumefaciens or its Ti-plasmid, or Cauliflower Mosaic Virus, have been used as vectors for this purpose.

Recently developed processes now render possible direct insertion of a gene into plant cells without using biological vectors [[9] Potrykus, I. et al., Plant Molec. Biol. Rep. 3, 117–128, (1985); [10] Shillito, R. D. et al., Bio/Technology 3, 1099–1103, (1985)].

These processes, which have become known by the catch phrase "direct gene transfer" render possible vector-free transformation of plant cells without the use of plant-infective systems such as, for example, plant-pathogenic bacteria, viruses, insects or fungi.

Consequently, all the limitations presented by the host-specificity of the pathogens no longer apply. The development of plants from transformed cells is not impaired by the use of the novel processes for transforming plant cells.

One of the main problems in the application of gene transformation resides in the difficulty in identifying the transformed cells or tissue.

The lower the transformation frequency in a gene transformation process, the more difficult and more complicated it is to find the few cell clones resulting from the transformed cells among the enormous number of clones that have not been transformed. The use of customary screening methods, therefore, is almost impossible or completely impossible if the transformation frequency is low unless the gene is a gene with a selective marker function (for example resistance to a specific substance). Consequently, a low transformation frequency in the case of genes that do not have a selectable marker function demands enormous expenditure.

Therefore, for transformations with genes not having a marker function, the customary screening methods for selecting transformed cell clones can be used efficiently and successfully only if the transformation frequency is of the order of $10^{-3}$ to $10^{-2}$. At present, these desired high transformation rates can be achieved only by using electroporation, possibly in conjunction with other processes for gene transfer used in microbiological research such as, for example, poly-L-ornithine or poly-L-lysine treatment, liposome fusion, DNA-protein complexing, charge modification on the protoplast membrane, fusion with microbial protoplasts or calcium phosphate correcipitation and, especially, polyethylene glycol treatment and the heat shock method [[10] Shillito et al., Bio/Technology 3, 1099–1103 (1985)]. By comparison, when using purely chemical process steps it has been possible hitherto to achieve reproducable transformation rates only of an order of magnitude of up to $10^{-1}$.

In electroporation, [[11] Neumann, E. et al., The EMBO Journal 7, 841–845 (1982), [10] Shillito et al., Bio/Technology 3, (1985)] protoplasts in a mannitol/calcium or a mannitol/magnesium solution are briefly acted upon by a voltage pulse of high intensity by discharging a capacitor across the suspension liquid. This causes a polarisation of the protoplast membrane and a reversible opening of pores in the membrane, facilitating transfer of the DNA into the cell.

This process, however, has numerous disadvantages and is subject to certain limitations.

First, to carry out transformation by electroporation, apparatus of relatively great complexity is necessary, which involves corresponding costs and a corresponding amount of work. Secondly, the use of this process is possible only within a very narrow limiting range owing to the high degree of sensitivity of plant protoplasts. In order to ensure the viability of transformed cells, certain parameters such as, for example, voltage, capacitance and field strength values, can therefore be varied only within these narrow limits (for example a voltage range of from 1400 to 1700 V) [[10] Shillito, R. D. et al., Bio/Technology 3, (1985)].

These disadvantages can, surprisingly, be overcome within the scope of the process according to the present invention by simple, purely chemical, process steps.

The investigations carried out within the scope of the present invention on the principles that are responsible for the taking up and integration of DNA into plant cells have let it become clear that the transformation process is dependent on a large number of mutually influencing parameters. Building upon these investigations, it is now possible by variation and optimal coordination of the parameters relevant to the transformation significantly so to increase the transformation frequency in comparison with conventional processes that the desired transformation rates of $10^{-1}$ to $10^{-2}$ and more mentioned at the beginning can be achieved easily.

By means of the process according to this invention, which is based on purely chemical measures, it is now possible not only for the transformation frequency but also, suprisingly, for the reproducibility and survival rate of the treated protoplasts, to be increased very significantly.

Whereas the maximum transformation frequencies hitherto obtainable with purely chemical processes were in the region of $10^{-5}$, it is now possible, using the process according to the invention, to achieve reproducible transformation frequencies of the order of up to a few percent, comparable to those of electroporation.

In contrast to electroporation, the improved process according to the invention is a method that can be carried out without special expenditure on apparatus thus making it more favourably priced and less labour-intensive. A further advantage compared with methods requiring electroporation resides in the novel possibility of now being able to transform large quantities of plant protoplasts at the same time.

When using the process according to the present invention there are no limitations comparable to those dicussed hereinbefore for the electroporation process in connection with the survival rate of the treated cells.

The determining parameters for the transformation according to the invention are variable over a wide range and do not impair the transformation efficiency or the viability of the treated protoplasts within this range.

Furthermore, after transformation using the process according to the invention, the entire protoplast population proves to be far less heterogeneous, both as regards the viability and the divisibility of the treated protoplasts, than is the case where transformation has been carried out by electroporation. When using the process according to this invention it is possible, for example, for survival rates of the treated protoplasts of 80% and above to be achieved easily, whilst at the same time their ability to divide, and thus the possibility of forming new colonies, is retained. When using electroporation, comparable values regarding the survival rate are, by contrast, only approximately 10%.

Contrary to expectations, it has now been found that the transformation frequency in direct gene transfer into protoplasts can be influenced by a large number of parameters, individually or combined, and that by correct selection and combination of only a few of these parameters or measures it is possible to achieve an optimum transformation rate with low technical expenditure and low expenditure of time. The following parameters proved to be essential:

1) DNA-sample: form, size, concentration, time of application,
2) carrier DNA: form, concentration, size
3) $Mg^{2+}$: concentration, time of application
4) plasma membranemodifying agent: concentration, time of application Of the factors essential for the process according to the invention it is especially the $Mg^{2+}$ concentration and the concentration of the plasma membrane-modifying agent that are of decisive importance for the increase in the transformation efficiency. A synergistic interaction is observed between these two factors, which subsequently results in a marked increase in the transformation frequency.

Also of importance are the time and the sequence of the application of the $Mg^{2+}$ ions, the modifying agent and the transforming DNA.

This decisive improvement and simplification of the process for direct gene transfer into plant protoplasts and ultimately for the production of genetically modified plants can be achieved by the following steps which are essential to the invention:

isolation of the protoplasts from plant material and, optionally, incubation of the isolated protoplasts in a suitable nutrient medium, resuspension of the isolated protoplasts in a standardised salt solution, transfer of the isolated protoplasts from the salt solution into an incubation medium, optimised for the transformation, that contains $Mg^{2+}$ ions, addition of the DNA to be inserted and of an agent that modifies the plasma membrane, incubation of protoplasts and DNA in the presence of a substance that modifies the plasma membrane, for a period that is sufficient for a penetration of the DNA into the protoplasts, separation of the treated protoplasts from the incubation solution and, if necessary, resuspension thereof in an aqueous $CaCl_2$ solution, separation of the protoplasts from the $CaCl_2$ solution, incubation in a culture medium suitable for the further development of the protoplasts and if desired, regeneration of complete transformed plants.

The present invention thus relates essentially to an improved process for transforming plant protoplasts and, if desired, to the production of whole, genetically modified plants by regeneration from the said transformed protoplasts, which process is characterised in that plant protoplasts are isolated from any plant tissue and, optionally, cultured in one of the nutrient media customarily used for culturing plant protoplasts;

before the actual transformation, the said protoplasts are preincubated at a temperature of from 4°° to 10° C. for from 20 minutes to 6 hours in a pre-incubation medium containing alkaline earth and/or alkali metal cations preferably $Ca^{2+}$, $K^+$ and/or $Na^+$ ions, and also a suitable carbon source;

the protoplasts are then separated from the pre-incubation medium and resuspended in the actual transformation medium which contains as an essential component from 0.1 to 60 mM, preferably from 10 to 30 mM, $Mg^{2+}$ ions, in the presence or absence of $Ca^{2+}$ ions;

directly thereafter a DNA sample, containing one or more genes under the control of expression signals active in plants and also a supporting DNA, is added to the transformation solution;

from a few seconds to 20 minutes, preferably from 0.1 to 10 minutes, later, an agent that modifies the plasma membrane is added;

the protoplasts and DNA sample are incubated in the said transformation solution for a period that ensures the incorporation of the DNA into the protoplasts; and if desired, whole plants are regenerated from the transformed protoplasts.

It is clear from this description that the transfer according to the invention of the new genes into the plant cells is carried out by direct means, without the use of a natural plant-infective system, such as a plant bacterium, a plant virus or transfer by insects or phytopathogenic fungi. In order to do this, the plant protoplasts to be transformed are treated directly with the gene to be transferred, as follows: first of all the protoplasts are introduced into a suitable solution and pre-incubated therein for a specific period, then the protoplasts together with the foreign gene are transferred into the actual transformation medium and are left there for a period that is sufficient for the foreign gene to be incorporated into the protoplasts.

The plant protoplasts used are preferably those of a single species of plant or of a systematic unit sub-ordinate to the species.

Isolated plant protoplasts that are suitable as a starting material for isolated cells and tissue can be obtained from any part of the plant such as, for example, from leaves, seedlings, stems, flowers, roots, pollen or embryos. Preferably, leaf protoplasts are used. The isolated protoplasts can also be obtained from cell cultures. Methods of isolating protoplasts can be found, for example, in [12] Potrykus, I. and Shillito, R. D., Methods in Enzymology 118, 449–578 (1986).

Suitable solutions in which the protoplasts are cultured are preferably osmotically stabilised culture media such as those customarily used for protoplast cultures.

Numerous culture media, which differ in their individual components or groups of such components, are already available. All media are, however, generally formulated in accordance with the following principle: they contain a group of inorganic ions in a concentration range of from approximately 10 mg/l to a few hundred mg/l (so-called macro-elements such as, for example, nitrate, phosphate, sulphate, potassium, magnesium, iron), a further group of inorganic ions in maximum amounts of a few mg/l (the so-called micro-elements such as, for example, cobalt, zinc, copper, manganese), and also a series of vitamins (for example inositol, folic acid, thiamine), an energy and carbon source such as, for example, saccharose or glucose, and also growth regulators in the form of natural or synthetic phytohormones from the auxin and cytokinin classes in a concentration range of from 0.01 to 10 mg/l. The culture media are, in addition, osmotically stabilised by the addition of sugar alcohols (for example mannitol) or sugars (for example glucose) or salt ions (for example $CaCl_2$), and are adjusted to a pH value of from 5.6 to 6.5.

A more detailed description of current culture media is to be found, for example, in [13] Koblitz, H., Methodische Aspekte der Zell- und Gewebezuchtung bei Gramineen unter besonderer Berucksichtigung der Getreide, (Aspects of methods of cell and tissue growth in Gramineae with special reference to cereals) Kulturpflanze XXII, 1974, 93–157.

Before the protoplasts are transferred into the actual transformation medium they are first of all pre-incubated in a medium that prepares them in an optimum manner for the subsequent transformation; the advantages of this are manifested in a clear increase in the achieved transformation and survival rates of the protoplasts treated.

With certain prerequisites, it is also possible to carry out the transformation directly in the said pre-incubation medium.

The said medium is a standardised salt solution that in addition to a suitable carbon source such as, for example, a sugar or sugar alcohol such as glucose or mannitol, contains various salts, for example NaCl, $CaCl_2$, KCl, in a concentration of from 1 mM to 200 mM. This salt solution advantageously has a pH value of from 5 to 8.

Shortly before the intended transformation, the protoplasts are transferred from the pre-incubation solution into the actual transformation medium. This medium is a mannitol solution that contains $Mg^{2+}$ ions in a concentration of from 0.1 mM to 60 mM, preferably in a concentration of from 10 mM to 30 mM. The pH value of the incubation solution is from pH 5.6 to pH 12, especially from pH 7 to pH 10.

Directly after the isolated protoplasts have been introduced into the incubation medium, the DNA sample is added in a concentration of from 2 μg/ml to 20 μg/ml, preferably in a concentration of from 5 μg/ml to 10 μg/ml.

The DNA, consisting of a structural gene and plant-active expression signals, is advantageously flanked by neutral DNA sequences (supporting DNA) that render possible the integration of the gene into the genomic DNA of the plant cell. It is advantageous to use the gene in linearised form. In the course of the experiments carried out, a supporting DNA concentration of from 50 μg/ml to 70 μg/ml at an average size of from 4 kb to 40 kb proved especially suitable.

It is furthermore advantageous for neutral DNA such as, for example, animal or plant DNA, lambda DNA, plasmid DNA, or any other DNA that is suitable for carrying out the process according to the invention, to be used in excess as carrier DNA in order to protect the gene from being degraded by nucleases.

From a few seconds to 20 minutes, preferably from 0.1 minute to 10 minutes, after the DNA has been added to the incubation solution, polyethylene glycol is added until a final concentration of from 10% to 30% has been reached. High transformation rates are achieved at a PEG concentration of from 20% to 28%.

Apart from polyethylene glycol however, it is also possible in the process according to the invention to use other higher alcohols or alcohol-type substances that likewise modify the protoplast membrane and that are used, for example, in the field of cell fusion. Examples of these are longer-chained, polyhydric alcohols such as polypropylene glycol (from 425 to 4000 g/mol), polyvinyl alcohol, or polyhydric alcohols in which some or all of the hydroxy groups are etherified, and also plant-compatible detergents customary in the agricultural field such as are described, for example, in the following publications:

[14] "McCutcheon's Detergents and Emulsifiers Annual" MC Publishing Corp., Ridgewood New Jersey, 1981; Stache, H., "Tensid-Taschenbuch", Carl Hanser Verlag, Munich/Vienna, 1981

If polyethylene glycol itself is used (as in Examples 1 and 2), it is preferably a polyethylene glycol having a molecular weight of from 1000 g/mol to 10000 g/mol, especially from 3000 g/mol to 8000 g/mol.

Of the afore-mentioned agents, the substance polyethylene glycol itself is preferred, especially a polyethylene glycol solution of the CMS type that has a relatively high proportion of $Ca^{2+}$ ions. [15) Negrutiu, I. et al., Theor. Appl. Genet. 72, 279–86, (1986a)].

A period of incubation with polyethylene glycol of from 20 minutes to 6 hours has proved especially advantageous for the course of the transformation.

After the treatment carried out in the manner indicated above, the protoplasts are resuspended in fresh culture medium, the cell density advantageously being adjusted to values of from $2\times10^4$ to $8\times10^4$ protoplasts per ml of culture medium.

If PEG is used in a concentration of >20% it is expedient, when transformation is complete, to dilute the protoplasts in stages with from 2 to 10 times the volume of a solution containing $Ca^{2+}$ ions, and thus to wash out any PEG residues present by subsequent sedimentation and resuspension in fresh culture medium.

An aqueous $CaCl_2$ solution with a $Ca^{2+}$ ion concentration of from 0.1M to 1.0M has proved especially advantageous for the transformation results.

The process according to the invention has practically unlimited application.

The present invention relates especially to chimaeric genetic constructions that possess as a central component one or more structural genes that code for novel useful and desirable properties and that are linked in an operable manner with expression signals that are functional in plant cells.

There is suitable for use in the process according to the invention especially any gene that is expressed in plant cells and that imparts to the plant a useful and/or desirable property such as, for example, an increased resistance to or tolerance of pathogens (for example phytopathogenic insects, fungi, bacteria, viruses etc.), herbicides, insecticides or other biocides, climatic influences and local peculiarities (for example heat, cold, wind, dryness, dampness, special extreme soil conditions, osmotic stress etc.), or an increased formation of reserve and stored substances in leaves, seeds, tubers, roots, stems etc..

The present invention also includes genes that code for pharmaceutically acceptable active substances such as, for example, alkaloids, steroids, hormones, immunomodulators and other physiologically active substances.

Thus, any structural gene of plant origin such as, for example, the zein gene [16) Wienand, U., et al., Mol. Gen. Genet. 182, 440–444 (1981)], of animal origin such as, for example, the TPA gene (tissue-type plasminogen activator gene; 17) Pennica, D., et al., Nature 301,214–221, (1983)], of microbial origin such as, for example, the NPT-II gene, or of synthetic origin such as, for example, the insulin gene [18) Stepien, P., et al., Gene 24, 289–297 (1983)]can be transferred into the genotype of plants provided that the structural gene is flanked by expression signals that are active in plants, it being possible for the expression signals to be of plant, animal, microbial or synthetic origin.

There are to be understood by "expression signals" within the scope of this invention especially promoter and termination sequences, but furthermore also other regulatory sequences in the 5'- and the 3'-non-translated regions that are situated upstream or downstream of the structural gene sequences.

The promoter sequences contain, inter alia, a recognition site for RNA polymerase, to which this enzyme is specifically bound and so initiates transcription.

Certain DNA sequences that occur frequently in procaryotic promoters are responsible for the binding affinity. These so-called "Consensus" sequences are found, as a rule, in the sequence region −10 to −30 relative to the ATG start codon of the structural gene. They are two hexanucleotide sequences, which are referred to as the "Pribnov-Schaller-Box", and the sequence of nucleotides within these sequences, as well as their spacing from each other, have a decisive influence on the affinity of the DNA polymerase to the promoter.

In eucaryotic cells, particular importance is attached in this connection to the so-called "TATA" box, a sequence rich in adenine and thymine that is located 20 to 30 nucleotides upstream from the transcription initiation site.

Suitable genes that can be used within the scope of the present invention are both homologous and heterologous gene(s) or DNA as well as synthetic gene(s) or DNA in accordance with the definition given within the scope of the present invention.

The coding DNA sequence can be constructed exclusively from genomic DNA, from cDNA or from synthetic DNA. Another possibility is the construction of a hybrid DNA sequence consisting of both cDNA and genomic DNA and/or synthetic DNA.

In that case the cDNA may originate from the same gene as the genomic DNA, or alternatively both the cDNA and the genomic DNA may originate from different genes. In any case, however, both the genomic DNA and/or the cDNA may each be prepared individually from the same or from different genes.

If the DNA sequence contains portions of more than one gene, these genes may originate from one and the same organism, from several organisms that belong to more than one strain, one variety or one species of the same genus, or from organisms that belong to more than one genus of the same or of another taxonomic unit (kingdom).

In order to ensure the expression of the said structural genes in the plant cell, the coding gene sequences must first of all be ligated in an operable manner with expression sequences capable of functioning in plant cells.

The transferred genes, consisting of structural gene and flanking expression signals, may be either naturally occurring genes or hybrid genes. The genes preferably used in the process according to the invention are those in which the expression signals are of animal or, especially, plant or synthetic, origin. Examples of such genes are:

a) complete genes from plants, consisting of the structural gene with its natural expression signals;
b) completely synthetic genes, consisting of a structural gene of synthetic origin flanked by expression signals of synthetic origin;
c) structural genes of plant origin, flanked by plant-active expression signals, the structural gene and expression signals originating from different species of plants;
d) structural genes of plant origin, flanked by expression signals of synthetic origin;
e) structural genes of animal, microbial or synthetic origin, flanked by expression signals of plant origin; or
f) structural genes of animal or microbial origin, flanked by expression signals of synthetic origin.

The hybrid gene constructions within the scope of the present invention thus contain, in addition to the structural gene(s), expression signals that include both promoter and terminator sequences as well as other regulatory sequences of the 3'- and 5'-non-translated regions.

More especially preferred are structural genes of bacterial origin, flanked by expression signals of plant origin, especially those originating from plant viruses.

Any promoter and any terminator that is capable of inducing the expression of a coding DNA sequence (structural gone) can be used as component of the hybrid gone sequence. Examples of suitable promoters and terminators are those of nopalin-synthase genes (nos), of octopine-synthase genes (ocs) and of Cauliflower Mosaic Virus genes (CaMV).

Preferred within the scope of this invention are the 35S and 19S expression signals of the CaMV genome that are isolated from the said genome and can be linked with the coding DNA sequence by means of molecular-biological methods such as are described, for example, in [19] Maniatis et al., 1982.

In accordance with the invention the starting material used for the 35S transcription control sequences may be, for example, the ScaI fragment of the CaMV strain "S", which comprises the nucleotides 6808–7632 of the gene map ([20] Frank Get al., 1980).

The 19S promoter and 5'-non-translated region is located on a genome fragment between the PstI site (position 5386) and the HindIII site (position 5850) of the CaMV gene map ([21] Hohn et al., 1982). The corresponding terminator and 3'-non-translated region is located on an EcoRV/BglII fragment between positions 7342 and 7643 of the CaMV genome.

The 19S promoter region is a typically eucaryotic promoter that is positioned before the coding region of the CaMV gene VI and is responsible for the expression of the gene VI product (virus coat protein).

Another effective representative of a promoter that functions in the plant cell and that can be used is an overproducing plant promoter. This type of promoter should, if it is linked in an operable manner with the gene sequence that codes for a desired gene product, be capable of bringing about the expression of the said gene sequence.

Over-producing plant promoters that can be used within the scope of the present invention include the promoter of the small subunit (ss) of ribulose-1,5-bis-phosphate-carboxylase from soybeans [22] [Berry-Lowe et al., *J. Mol. and Appl. Genet.*, 1: 483–498 (1982)] and the promoter of chlorophyll-a/b-binding protein. These two promoters are known for the property of being induced by light in eucaryotic plant cells [see, for example, [23] *Genetic Engineering of Plants, an Agricultural Perspective*, A. Cashmore, Plenum, New York 1983, page 29–38; [24] Coruzzi G. et al., *The Journal of Biological Chemistry*, 258:1399 (1983) and [25] Dunsmuir, P. et al., *Journal of Molecular and Applied Genetics*, 2: 285 (1983)].

The expression signals of gene VI of the Cauliflower Mosaic Virus have proved especially advantageous for use according to the present invention.

Especially preferred within the scope of this invention are the expression signals of the CaMV strain CM 1841, the complete DNA sequence of which is described in [26] Gardner et al., 1981.

The hybrid genes are manufactured according to microbiological processes that are known per se, the reading frame of the code for the proteins to be produced by the plant cell being retained. Such methods are known and are described, for example, in the following publications: [19] "Molecular Cloning", Maniatis, T., Fritsch, E. F. and J. Sambrook, Cold Spring Harbor Laboratory, 1982, and [27] "Recombinant DNA Techniques", Rodriguez, R. L. and R. C. Tait, Addison-Wesley Publishing Comp., London, Amsterdam, Don Mills. Ontario, Sydney, Tokyo, 1983.

For the integration of the foreign gene into the genomic DNA of the plant cell it is advantageous if the gene, consisting of structural gene and plant-active expression signals, is flanked by neutral DNA sequences (supporting DNA). The supporting DNA can in this case consist of two linear DNA strands, so that the construction to be inserted into the plant cell is a linear DNA molecule. The DNA sequence produced for the gene transfer may, however, alternatively have a ring-shaped structure (plasmid structure). Such plasmids consist of a DNA strand into which the foreign gene with the expression signals has been integrated. The supporting DNA may be of synthetic origin, or may be obtained from naturally occurring DNA sequences by treatment with suitable restriction enzymes. Suitable supporting DNAs are therefore, for example, naturally occurring plasmids that have been opened by a selective restriction enzyme. An example of such a plasmid is the freely obtainable plasmid pUC8 (described in [28] Messing, J. and J. Vieira, Gene 1–9, 269–276, 1982). It is also possible to use as supporting DNA fragments of naturally occurring plasmids. For example, the deletion mutant for gene VI of the Cauliflower Mosaic Virus can be used as supporting DNA.

The probability of genetic transformation of a plant cell can be increased by various factors. As is known from tests with yeast, the number of successful and stable gene transformations increases 1) as the number of copies of new genes per cell increases,
2) on combination of a replication signal with the new gene, and also
3) on combination of integration sequences with the new gene.

Consequently, the process according to the invention can be used with particular advantage if the transferred gene is combined with replication and/or integration sequences that are active in plant cells.

The expression of a gene in a plant cell is dependent on the frequency of transcription of the gene into a messenger RNA sequence. It is therefore similarly of advantage if the new gene is combined with an enhancer signal amplifying this transcription. Attention is drawn especially to those processes in which a gene that has been combined with replication, integration and enhancer signals that are active in plant cells is transferred.

Furthermore, it is of great advantage as regards the processing technology if the transferred gene has a selective marker function, that is to say that the transformed plant cells can be separated from the non-transformed cells by a controlled selection. Such a marker function renders possible an efficient mode of operation, since it is necessary to regenerate to calli or complete plants by customary microbiological measures only those plant cells in whose genotype there is a gene to be expressed that permits marker-specific selection measures to be used.

Whilst protoplasts, cell culture cells, cells in plant tissues, pollen, pollen tubes, ovules, embryo-sacs or zygotes, and embryos in various stages of development, may be mentioned as examples of suitable plant cells that can be used as starting materials for transformation, protoplasts are preferred since they can be used directly without further pre-treatment.

The present invention therefore also relates to the transformed protoplasts resulting from the process according to the invention and to the plant cells, cell aggregates, embryos, plants and seeds resulting from these, and also to the descendants thereof that possess the new genes obtained as a consequence of the transformation and that have the advantageous properties resulting therefrom.

Also included are all hybridisation and fusion products of plant material transformed in accordance with the invention that possess the new genes obtained as a consequence of the transformation and that have the advantageous properties resulting therefrom.

The process according to the invention is suitable for the transformation of all plants, especially those from the systematic groups Angiospermas and Gymnospermae.

The Gymnospermae that are of particular interest are the plants from the Coniferae class.

The Angiospermae that are of particular interest, apart from deciduous trees and shrubs, are plants of the Solanaceae, Cruciferae, Compositae, Liliaceae, Vitaceae, Chenopodiaceae, deciduous trees and shrubs, are plants of the Solanaceae, Cruciferae, Compositae, Liliaceae, Vitaceae, Chenopodiaceae, Rutaceae, Alliaceae, Amaryllidaceae, Asparagaceae, Orchidaceae, Palimae, Bromeliaceae, Riboaceae. Theaceae, Musaceae or Gramineae families and of the order Leguminosae and especially of the Papilonaceae family. Representatives of the Solanaceae, Cruciferae and Gramineae families are preferred.

Worthy of special mention are plants of the genera Nicotiana, Petunia, Hyoscyamus, Brassica and Lolium such as, for example, *Nicotiana tabacum, Nicotiana plubagenifolia, Petunia hybrida, Hyoscyamus muticus, Brassica napus, Brassica rapa* and *Lolium multiflorum*.

Cultivated plants with high yields such as maize, rice, wheat, barley, rye, oats and millet are especially the object of efforts in the field of transformation of plant cells.

All plants that can be produced by regeneration from protoplasts can also be transformed using the process according to the invention. It has not been possible hitherto for representatives of the Gramineae family (grasses), which also includes cereals, to be manipulated genetically. It has now been demonstrated that with the aforedescribed method of direct gene transformation it is also possible for Gramineae protoplasts, that is to say also cereal cells, to be transformed genetically. Similarly, transformation of the cultivated plants of the genera Solanum, Nicotiana, Brassica, Beta, Pisum, Phaseolus, Glycine, Helianthus, Allium, Avena, Hordeum, Oryzae, Setaria, Secale, Sorghum, Triticum, Zea, Musa, Cocos, Cydonia, Pyrus, Malus, Phoenix, Elaeis, Rubus, Fragaria, Prunus, Arachis, Panicum, Saccharum, Coffea, Camellia, Ananas, Vitis or Citrus is possible and desired, although the total yields and total cultivated areas worldwide for these are lower.

The regeneration of protoplasts kept in culture to whole plants is described in [29] Evans et al., "Protoplast Isolation and Culture", in *Handbook of Plant Cell Culture*, 1: 124–176 (MacMillan Publishing Co. New York 1983); [30] MR Davey, "Recent Developments in the Culture and Regeneration of Plant Protoplasts", *Protoplasts* 1983—Lecture Proceedings, page 19–29, (Birkhäuser, Basle 1983); [31]pJ Dale, "Protoplast Culture and Plant Regeneration of Cereals and Other Recalcitrant Crops", in *Protoplasts* 1983—Lecture Proceedings, page 31–41, (Birkhäuser, Basle 1983); and [32] H Binding, "Regeneration of Plants", in *Plant Protoplasts*, page 21–37, (CRC Press, Boca Raton 1985) and in [12]Potrykus I and Shillito RD, *Methods in Enzymology*, Vol. 118, Plant Molecular Biology, eds. A. and H. Weissbach, Academic Press, Orlando, 1986.

The regeneration processes differ from plant species to plant species. In general, however, first of all a suspension of transformed protoplasts, cells or tissue that contains numerous copies of the inserted gene is produced. Using such a suspension it is then possible to carry out the induction of the embryo formation. The development of the embryos is allowed to advance to the stage of maturity and germination, as is the case also with naturally occurring embryos. As a rule, however, the protoplasts are stimulated in one of the known culture media to divide and form cell walls. Ultimately, callus cultures result which can be induced to form roots and shoots by treatment with certain active ingredients such as, for example, auxins and cytokinins. Apart from these growth substances, the culture media as a rule contain various amino acids. It has proved advantageous to add glutamic acid and proline to the medium, especially in the case of species such as maize and alfalfa. The formation of roots and shoots generally occurs simultaneously.

The plantlets obtained in this manner can then be transferred into soil and further cultivated in the same manner as normal seedlings.

An efficient regeneration depends especially on the medium, on the genotype and on the previous history of the culture. If these three variables are adequately controlled, then the regeneration is completely reproducible and repeatable.

In view of new developments in the field of in vitro cultivation of plants, especially in the field of plant regeneration, it has since become possible, also in the case of representatives of the Gramineae family, to regenerate whole plants starting from plant protoplasts. Examples of regeneration experiments that have been carried out successfully with Gramineae are described, inter alia, in [33] Abdullah, R et al., *Bio/Technology*, 4: 1087–1090, 1986, [34] Fujimara, T., et al., *Plant Tissue Culture Lett*, 2: 74–75, 1985, [35] Toriyama, K. et al., *Theor Appl. Genet.*, 73: 16–19, 1986, [36] Yamada, Y., et al., *Plant Cell Rep.*, 5: 85–88, 1986 (rice) and also in the pending U.S. patent application having the Ser. No. 056,506, which was filed on 24th Jun. 1987 under the title "Regeneration of *Zea mays* plants from protoplast".

It is therefore also possible to use the following plants within the scope of the present invention: Lolium, Zea, Triticum, Sorghum, Saccharum, Bromus, Oryzae, Avena, Hordeum, Secale and Setaria.

Transformed genes can be detected in a manner known per se, for example by hybridisation analyses and molecular-biological investigations which include, especially, Southern blot analysis and enzyme activity tests.

In hybridisation analysis, the mature plants, which have been grown from transformed plant cells, are first of all crossed with themselves for the purpose of producing seeds. Some of the seeds contain the inserted genes that code for a new and desirable property in a ratio that corresponds exactly to the established laws of heredity. These seeds can be used to produce plants with new and desired properties.

Homozygous lines can be obtained by repeated self-fertilization and the development of inbred lines. These inbred lines can then be used, in turn, for the development of hybrids. In this process, one inbred line is crossed with another inbred line.

The present invention also relates to parts that can be obtained from regenerated plants, such as, for example, flowers, seeds, leaves, branches, fruits inter alia, provided that these parts contain transformed cells. Progeny (including hybrid progeny), varieties and mutants of the regenerated plants also form a part of this invention.

The Southern blot analysis can be carried out, for example, as follows: DNA taken from the transformed cells or protoplasts is, after treatment with restriction enzymes, subjected to electrophoresis in 1% agarose gel, transferred onto a nitrocellulose membrane [[37] Southern, E. M., J.Mol.Biol. 98, 503–517 (1975)] and hybridised with the DNA to be used for detection, which has been subjected to a nick-translation [38) Rigby, W. J., Dieckmann, M., Rhodes, C. and P. Berg, J.Mol.Btol. 113, 237–251 (1977)] (DNA-specific activity from $5\times10^8$ to $10\times10^8$ c.p.m/µg). The filters are then washed three times for an hour each time with an aqueous solution of 0.03M sodium citrate and 0.3M sodium chloride at 65° C. The hybridised DNA is rendered visible by blackening an X-ray film for from 24 to 48 hours.

An investigation of the enzyme activity can be carried out as follows [explained in detail by a test on aminoglycoside phosphotransferase (enzyme for canamycin-specific phosphorylation)]: portions of calli or leaves (from 100 to 200 mg) are homogenised in 20 µl of extraction buffer in an Eppendorf centrifugation tube. The buffer is a modification of the buffer used by [5)] Herrera-Estrella, L., DeBlock, M., Messens, E., Hernalsteens, J.-P., Van Montagu, M. and J. Schell, EMBO J. 2, 987–995 (1983), from which albumin from ox blood has been omitted and to which 0.1M sucrose has been added. The extracts are centrifuged for 5 minutes at 12,000 g and bromophenol blue is added to the supernatant phase until a final concentration of 0.004% is reached. The proteins are separated from 35 µl of the supernatant phase by electrophoresis in a 10%, non-denaturing polyacrylamide gel, The gel is covered with an agarose gel containing canamycin and γ32P-labelled ATP and incubated, and the phosphorylated reaction products are transferred onto Whatman-p81-phosphocellulose paper. The paper is washed six times with deionised water of 90° C. and then autoradiographed.

The following Examples serve to illustrate the present invention in detail but do not imply any limitation. They describe the construction of a hybrid gene and its incorporation into supporting DNA sequences having a cyclic character, the transfer of this hybrid gene into plant cells, the selection of the transformed plant cells and the regeneration of whole plants from the transformed plant cells, as well as their hybridisation-genetic and molecular-biological analyses.

In the Examples that follow the following abbreviations are used:

Media

HeNa;F [10 mM Hepes, pH 7.1, 5 mM CaCl2, 150 mM NaCl, 0.2M mannitol; [39)] Fromm, M. et al., (1985)]
K3 [0.1 mg/l 2.4 D, 1.0 mg/l NAA, 0.2 mg/l BAP; [40)] Shillito, R. D. et al. (1981); [41)] Nagy, J. I. and Maltga, P., (1976)]
Ka$_1$AO [[42)] Installe, P. et al., (1985)]
LS [[43)] Linsmaier, E. M., Skook, F., Phystologia Plantatum 18, 100–127, (1955)]
MaCa [0.4M mannitol, 15 mM CaCl$_2$x2H$_2$O, pH 5.6]
MaMg [from 0.4 to 0.5M mannitol, 15 mM MgCl$_2$, 0.1% MES, pH 5.6]
M [[42)] Installe, P. et al., (1985)]
MAP$_1$AO [[42)] Installe, P. et al., (1985)]
MDs [[44)] Negrutiu, I. et al., (1983)]
RP [[42)] Installe, P. et al., (1985)]
R'SA [[42)] Installe, P. et al., (1985)]
T [[45)] Nitsch, J. P. and C. Nitsch, (1969)]
W$_5$ [154 mM NaCl, 125 mM CaCl$_2$x2H$_2$O, 5 mM KCl, 5 mM glucose, pH from 5.6 to 6.0; [46)] Menczel et al., (1981)]

Chemicals

BAP benzylaminopurine
2,4 D (2,4-dichlorophenoxy)acetic acid
NAA naphthylacetic acid
ethylenediamine-N,N,N',N'-tetraacetic acid
EDTA
PEG CMS polyethylene glycol of the CMS type [[15)] Negrutiu, I. et al., (1986a)]
PEG 6R polyethylene glycol of the R-type [[10)] Shillito, R. D. et al., (1985)]
Tris-HCl α,α,α-tris-(hydroxymethyl)-methylamine-hydrochloride
NPT-II gene neomycin-3'-phosphotransferase gene, type II Tables ATF absolute transformation frequency
GPPL total number of protoplasts
RTF relative transformation frequency
UE surviving protoplasts after completion of transformation treatment
ZT number of transformants The percentages given in the following Examples are weight/volume percentages (w/v; volumetric weight).

BRIEF DESCRIPTION OF THE FIGURES

Graph A

Curve a: *N. tabacum* SR$_1$

Curve b: *N plumbaginifolia*

The semi-logarithmic scale of the MgCl$_2$ concentration (abscissa) should be noted. The PEG concentration in this case is 20% (w/v).

Graph B

Curve a: 15 mM MgCl$_2$

Curve b: 30 mM MgCl$_2$

Example 1

Construction of plasmid pABDI

Figure 1:
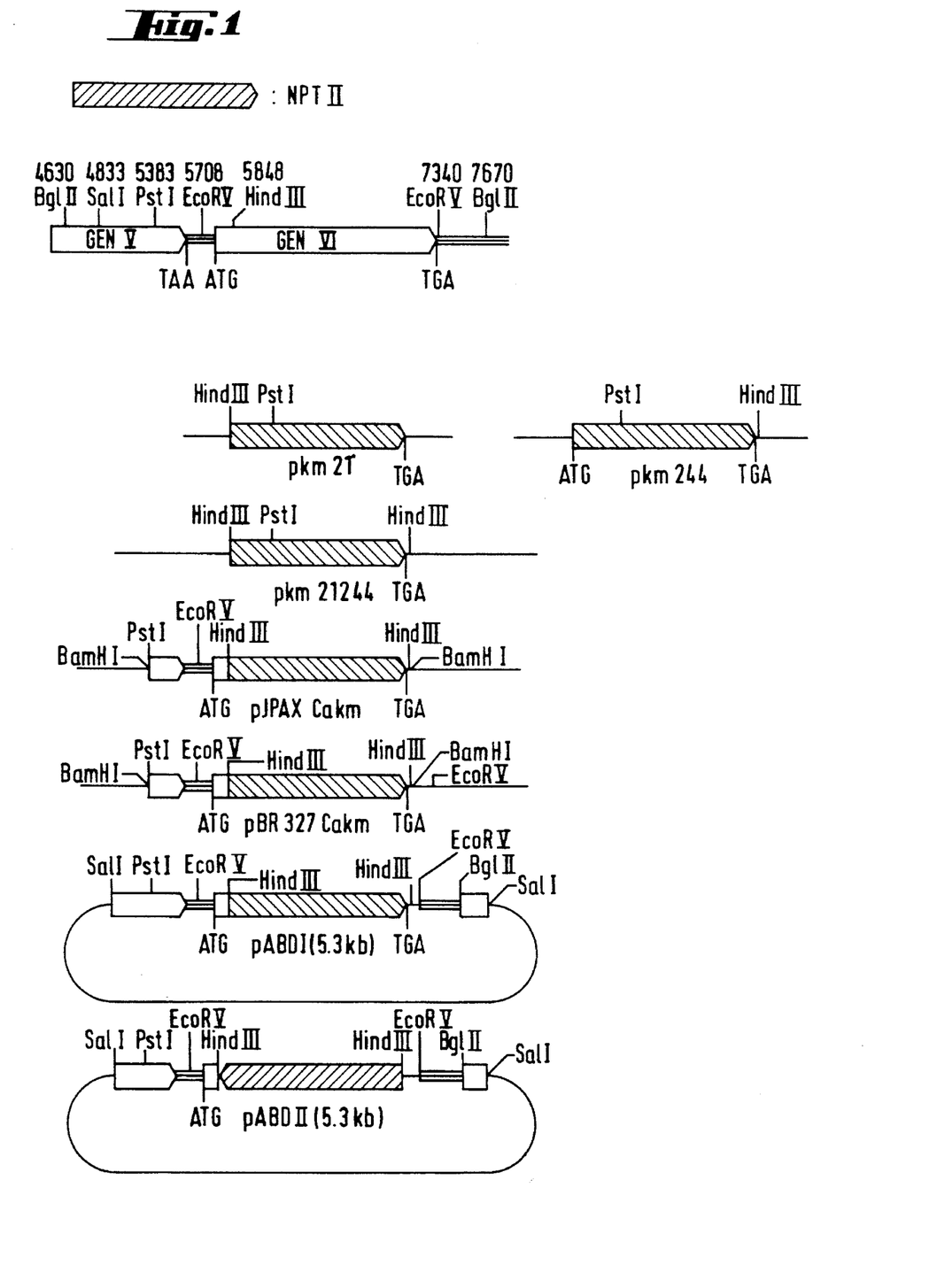
FIG. 1 shows the construction of the plasmid vectors pABD I and pABD II containing the NPT-II structural gene.

The freely accessible plasmids pkm 21 and pkm 244 [[47)] Beck, E., et al., Gene 19, 327–336 (1982)] are cleaved with the restriction endonuclease PstI. The plasmid fragments, which are used for recombination, are purified by electrophoresis in 0.8% agarose gel. Plasmid pkm 21244, obtained by joining the fragments, contains a combination of the 5'- and 3'-Bal 31 deletions of the NPT-II gene, as described by [47)] Beck et al. in Gene 19, 327–336 (1982). In order to join the promoter signal of the Cauliflower Mosaic Virus with the HindIII fragment of plasmid pkm 21244, coupling plasmid pJPAX is constructed. Coupling plasmid pJPAX is obtained from plasmids pUC8 and pUC9 [[28)] Messing, J. and J. Vieira, Gene 19, 269–276 (1982)]. 10 base pairs of the coupling sequence of plasmid put9 are separated by cleaving at the HindIII and the SalI sites and subsequently making up the sticky ends using the polymerase-I-Klenow fragment [[48)] Jacobsen, H., et al., Eur. J. Biochem. 45, 623, (1974)] and joining the polynucleotide chain, as a result of which the HindIII site is produced again. A synthetic coupling element of 8 base pairs (XhoI) is inserted at the SmaI site of this separated coupling sequence. The recombination of the suitable XorI and HindIII fragments of plasmid pUC8 and of modified plasmid put9 produces plasmid pJPAX having a partially asymmetric coupling sequence with the following successive restriction sites: EcoRI, SmaI, BamHI, SalI, PstI, HindIII, BamHI, XhoI and EcoRI. The CaMV gene VI promoter region, which is ligated to the NPT II structural gene, originates from the genome of CaMV strain CM4 184, a variant of the CaMV strain CM 1841, the complete nucleotide sequence of which is described in [26] Gardner RC et al., 1981. The CaMV promoter region is cloned in the 6kb cosmid pHC79, a derivative of the *E. coli* plasmid pBR322 ([49] Hohns B. and Collins J., 1980), the CaMV genome and cosmid pHC79 being cleaved with Bst II and the resulting fragments being ligated to one another. The 5'-expression signal of the Cauliflower Mosaic Virus gene VI and the HindIII fragment of the NPT-II gene are joined in plasmid pJPAX by inserting the promoter region of the Cauliflower Mosaic Virus gene VI between the PstI site and the HindIII site. The resulting plasmid is cleaved at the single HindIII site and the HindIII fragment of plasmid pkm 21244 is inserted into this incision site in both directions of orientation, resulting in plasmids pJPAX Cakm$^+$ and pJPAX Cakm. In order to create an EcoRV sequence in the vicinity of the 3'-termination signal of the NPT-II hybrid gene, a BamHI fragment of plasmid pJPAX Cakm$^+$ is inserted into the BandtI site of plasmid pBR 327 [[50] Soberon, X. et al., Gene 9, 287–305 (1980)]. Plasmid pBR 327 Cakm is obtained. The EcoRV fragment of plasmid pBR 327 Cakm, which contains the new DNA construction, is used to replace the EcoRV region of the Cauliflower Mosaic Virus Gene VI that has been cloned at the SalI site in plasmid pUC8, as a result of which the protein-coding DNA sequence of the NPT-II gene is under the control of the 5'- and 3'-expression signals of the Cauliflower Mosaic Virus gene VI. The resulting plasmids are designated pABDI and pABDII (cf FIG. 1).

Example 2

Transformation of protoplasts of Nicotiana tabacum c.v. Petit Havanna SRIby transferring the NPT-II gene as part of plasmid pABDI with the aid of Mg$^{2+}$/PEG treatment Tobacco protoplasts of *Nicotiana tabacum* c.v. Petit Havanna are produced according to conventional processes from a tobacco suspension culture ([12] Potrykus I and Shillito R D, *Methods in Enzymology*, vol. 118, Plant Molecular Biology, eds. A. and H. Weissbach, Academic Press, Orlando, 1986). Completely unfolded leaves are removed under sterile conditions from 6-week-old shoot cultures and thoroughly wetted with an enzyme solution of the following composition: Enzyme solution:

H$_2$O 70 ml sucrose 13 g macerozyme R 10 1 g cellulase 2 g

"Onozuka" R 10 (Yakult Co. Ltd., Japan) Drisellase (Chemische Fabrik Schweizerhalle, Switzerland) 0.13 g 2(n-morpholine)-ethanesulphonic acid (MES) 0.5 ml pH 6.0

Leaves are then cut into squares from 1 to 2 cm in size and the squares are floated on the above-mentioned enzyme solution. They are incubated overnight at a temperature of 26° C. in the dark. This mixture is then gently shaken and incubated for a further 30 minutes until digestion is complete.

The suspension is then filtered through a steel sieve having a mesh width of 100 μm, rinsed thoroughly with 0.6M sucrose (MES, pH 5.6) and subsequently centrifuged for 10 minutes at from 4000 to 5000 rpm. The protoplasts collect on the surface of the medium which is then removed from under the protoplasts, for example using a sterilised injection syringe.

The protoplasts are resuspended in a K3A medium [sucrose (102.96 g/l; xylose (0.25 g/l); 2,4-dichlorophenoxyacetic acid (0.10 mg/l); 1-naphthylacetic acid (1.00 mg/l); 6-benzylaminopurine (0.20 mg/l); pH 5.8][[12] Potrykus I and Shillito, R. D. et al., 1981] that contains 0.4M sucrose.

To carry out the transformation experiments, the protoplasts are first of all washed, counted and then resuspended, at a cell density of from 1 to 2.5×10$^6$ cells per ml, in a W$_5$ medium [154 mM NaCl, 125 mM CaCl$_2$x2H$_2$O, 5 mM KCl, 5 mM glucose, pH 5.6; [46] Menczel, L. et al. (1981)], which ensures a high survival rate of the isolated protoplasts. After incubation for 30 minutes at from 6° to 8° C., the protoplasts are then used for the transformation experiments.

Shortly before the actual transformation of the isolated protoplasts, the W$_5$ medium is replaced by the actual transformation medium. This is a mannitol/magnesium solution (MaMg-soln: 0.4–0.5 mM mannitol, 0.1% MES (morpholinethanesulphonic acid), pH 5.6] with a Mg$^{2+}$ concentration of from 12 to 16 mM. The protoplasts are first of all separated from the W$_5$ solution by centrifugation for 5 minutes at 100 g and resuspended in the MaMg medium (0.3 ml). 65 μl of an aqueous DNA solution, containing from 5 to 10 μg of plasmid pABDI and 50 μg of calf's thymus carrier DNA are then added to this suspension. The latter DNA is a neutral carrier DNA without a transforming insert, which is added in excess to this mixture to protect the DNA to be transformed against nuclease digestion. After a period of approximately from 0.1 to 10 minutes after the addition of the DNA, an aqueous 40% polyethylene glycol solution (w/v) is added until a final concentration of from 24 to 28% (w/v) is reached. The use of PEG of the CMS type has proved especially advantageous. This is a Ca$^{2+}$-containing 0.4M mannitol solution [0.1M Ca(NO$_3$)2.4H$_2$O], which contains PEG of a molecular weight of approximately from 1000 to 6000 in a final concentration of 40% (w/v). The pH value of this solution is from pH 7 to 9 [[15] Negrutiu, I. et al., (1986a)].

In the case of *Nicotiana tabacum* c.v. Petit Havanna SR1, PEG CMS 4000 is preferably used. The pH value of the transformation medium is subsequently adjusted to a value of pH 7. This mixture is incubated for 30 minutes at 26° C. with occasional shaking.

If high PEG concentrations of >20% are used, dilution in stages with from 3 to 5 times the volume of a 0.2M CaCl$_2$ solution is advantageous. The protoplasts treated in the manner indicated are then centrifuged off (5 minutes at 100 g) and resuspended in fresh Ka medium (0.3 ml protoplast solution in 10 ml of fresh K$_3$ medium).

The further incubation is carried out in 10 ml portions in 10 cm diameter petri dishes at 24° C. in the dark, the population density being from 4 to 8×10$^4$ protoplasts per ml. After 3 days, the culture medium is diluted with 0.3 parts by volume of K$_3$ medium per dish and incubation is continued for a further 4 days at 24° C. and 3000 lux of artifical light. After a total of 7 days, the clones that have developed from the protoplasts are embedded in nutrient medium that contains 50 mg/l of kanamycin and has been solidified with 1% agarose, and are cultured at 24° C. in the dark in accordance with the "bead-type" culturing method [[51] Shillito, R. D. et al., Plant Cell Reports, 2, 244–247 (1983)]. The nutrient medium is replaced every 5 days by a fresh amount of the same nutrient solution.

Example 3

Regeneration of kanamycin-resistant N. tabacum c.v. Petit Havanna SR1

After from 3 to 4 weeks continuous culturing in kanamycin-containing nutrient medium, the resistant calli that are from 2 to 3 mm in diameter are transplanted onto LS culture medium [[43]] Linsmaier, E. M. and Skook, F., Physiol. Plant 18, 100–127 (1965)], that has been solidified with agar and that contains 0.05 mg/l of 2,4-dichlorophenoxyacetic acid, 2 mg/l of 1-naphthylacetic acid, 0.1 mg/l of 6-benzylaminopurine, 0.1 mg/l of kinetin and 75 mg/l of kanamycin. Shoot induction on LS medium containing 150 mg/l of kanamycin and 0.2 mg/l of 6-benzylaminopurine, and then root formation on T medium [[45]] Nitsch, Y.P and C. Nitsch, Science 163, 85–87 (1969)]results in kanamycin-resistant *Nicotiana tabacum* plants of the variety Petit Havanna SR1.

Example 4

Transformation of protoplasts of Nicotiana plumbaginifolia by transferring the NPT-II gene as part of plasmid pABDI with the aid of $Mg^{2+}$/PEG treatment The isolation of the protoplasts and the pre-incubation of the protoplasts provided for the actual transformation experiments is carried out in a manner exactly analogous to the process described for *Nicotiana tabacum* SR1.

The actual transformation of the *N. plumbaginifolia* protoplasts pretreated in the manner indicated is carried out in a mannitol/magnesium solution [MaMg soln: 0.4 to 0.5 mM mannitol, 0.1% MES (morpholinethanesulphonic acid), pH 5.6] with a $Mg^{2+}$ ion concentration of from 22 to 27 mM. After the addition of an aqueous DNA solution (65 µl) containing from 5 to 10 µg of plasmid pABDI and 50 µg of calf's thymus carrier DNA, an aqueous 40% polyethylene glycol solution (w/v) is added until a final concentration of from 18 to 22% (w/v) is reached.

The period of time between the addition of the DNA and the application of PEG is, as a rule, only approximately from 0.1 to 10 minutes. The use of PEG CMS 4000 also proves especially advantageous in the case of *Nicotiana plumbaginifolia* for achieving high transformation rates. The pH value of the transformation medium is subsequently adjusted to pH 7. The transformation solution is then incubated for approximately 30 minutes at a temperature of 26° C. with occasional shaking of the mixture.

The isolated protoplasts are first of all cultured for a period of from 4 to 12 days in a medium with a high hormone concentration [($KA_1AO$ medium, [42]Installe, P. et al., J. Plant Physiol. 119, 443–454, (1985)] at a cell density of from 2 to $3 \times 10^4$ protoplasts/ml.

After the development of cell aggregates, the surviving colonies are selected, counted and suspended in a strong dilution (from 0.5 to $2 \times 10^3$ colonies/ml) in a MDs medium [[44]] Negrutiu, I. et al., Theor. Appl. Genet. 66, 341–347, (1983)] or a $MAP_1AO$ medium [[42]]Installe, P. et al., (1985)] with a low hormone content, containing from 20 to 40 mg/l of kanamycin sulphate. The colonies are then embedded in agar (1% agarose) and cultured at a temperature of 24° C. in the dark in accordance with the "bead-type" culturing method [[51]] Shillito, R. D. et al., (1983)]. The nutrient medium is replaced every 5 days by a fresh amount of the same culture solution.

Example 5

Regeneration of kanamycin-resistant *N. plumbaginifolia* plants

After they have been cultured for from 3 to 4 weeks, the resistant calli that have reached a diameter of from 2 to 5 mm are selected and cultured for a further 3 to 5 weeks on solid media containing 50 mg/l of kanamycin.

Whole plants are regenerated in accordance with the details in [42]Installe, P. et al. (1985) by transferring the resistant calli from a RP medium to a R'SA and/or a M medium.

Example 6

Detection of the NPT-II gene in the plant genotype 0.5 g of callus from the transformed cell cultures or of leaf tissue from plants regenerated therefrom are homogenised at 0° C. in 15% saccharose solution pH 8.0 containing 50 mmol/l of ethylenediamine-N,N,N',N'-tetraacetic acid, (EDTA), 0.25 mol/l of sodium chloride and 50 mmol/l of $\alpha,\alpha,\alpha$-tris-(hydroxymethyl)-methylamine hydrochloride (TRIS-HCl). The cell nuclei are roughly separated off by centrifuging the homogenisate for 5 minutes at 1000 g. The cell nuclei are resuspended in 15% saccharose solution pH 8.0 containing 50 mmol/l of EDTA and 50 mmol/l of TRIS-HCl, sodium dodecylsulphate is added until a final concentration of 0.2% is reached, and the whole is heated for 10 minutes at 70° C. After the mixture has been cooled to 20° to 25° C., potassium acetate is added until a concentration of 0.5 mol/l is reached. This mixture is incubated for 1 hour at 0° C. The resulting precipitate is separated by centrifugation (15 minutes at 4° C. in a microcentrifuge). The DNA is precipitated from the supernatant liquid at from 20° to 25° C. by adding 2.5 times the volume of ethanol. The isolated DNA is dissolved in a solution of 10 mmol of TRIS-HCl containing 10 µg/ml of ribonuclease A, incubated for 10 minutes at 37° C., proteinase K is added until a concentration of 250 µg/ml is reached, and the whole is incubated for a further hour at 37° C. Proteinase K is removed by phenol and chloroform/isoamyl alcohol extraction processes. The DNA is precipitated from the aqueous phase by the addition of 0.6 parts by volume of a 0.6 molar solution of sodium acetate in isopropanol, and dissolved in 50 µl of a solution pH 7.5 containing 10 mmol/l of TRIS-HCl and 5 mmol/l of EDTA. By means of this preparation, DNA sequences predominantly containing more than 50,000 base pairs are obtained. Restriction of this DNA with EcoRV endonuclease, hybridisation of the fragments with radioactively labelled HindIII fragments of the NPT-II gene and comparison with plasmid pABDI demonstrates, in a Southern blot analysis, the presence of the NPT-II gene in the cell nucleus DNA of the transformed *Nicotiana tabacum* and *Nicotiana plumbaginifolia* cells.

Results Section

In the following, the transformation results achieved are discussed in relation to various transformation parameters.

The transformation rates achieved are quoted in the form of "relative transformation frequencies" (RTF) and of "absolute transformation frequencies" (ATF).

The "relative transformation frequencies" relate to the ratio between the number of transformants and the surviving fraction (that are able to form colonies) of a non-selectively cultured protoplast population. The "absolute transformation frequency", on the other hand, is defined as the ratio between the same number of transformants and the original number of protoplasts that had been characterised as living before the transformation.

A comparison between ATF and RTF gives a good picture of the survival rate of the protoplasts after the individual transformation and selection steps have been carried out. Influence of structure and concentration of the DNA used on the transformation rate

TABLE 1

Influence of the DNA structure and the ratio of the concentration of plasmid DNA (pABDI) to carrier DNA on the transformation rates (RTF and ATF) in the case of *Nicotiana plumbaginifolia* protoplasts. The transformation experiments were carried out in a MaCa solution at a PEG CMS4 concentration of 13%

| DNA concentration [µg/ml] | GPPL $\times 10^6$ | UE $\times 10^4$ | ZT | RTF $\times 10^{-4}$ | ATF $\times 10^{-4}$ |
|---|---|---|---|---|---|
| linear pBADI | | | | | |
| 10 + 20 | 2 | 45 | 4 | 0.085 | 0.02 |
| 10 + 50 | 2 | 49.6 | 23 | 0.464 | 0.12 |
| 50 + 10 | 2 | 46.4 | 1 | 0.022 | 0.005 |
| circular pABDI | | | | | |
| 10 + 50 | 2 | 45.4 | 0 | <0.01 | <0.005 |
| 50 + 10 | 2 | 41.6 | 0 | <0.01 | <0.005 |

The influence of the DNA structure on the transformation rates may be demonstrated using as an example *Nicotiana plumbaginifolia* (Tab. 1).

It becomes clear in the course of the transformation experiments carried out that distinctly higher transformation frequencies can be achieved with linear DNA than with a circular DNA. The transformation rates achieved in the case of linear DNA are up to two powers of ten higher than the corresponding values achieved using a circular DNA.

Table 1 demonstrates clearly that not only the DNA structure but also the ratio of plasmid DNA to added carrier DNA has a bearing on the transformation frequencies that can be achieved.

The best results are achieved when the carrier DNA is clearly in excess in relation to the plasmid DNA, a ratio of 10:50 (plasmid DNA:carrier DNA) being especially advantageous.

The results achieved here confirm results that it has previously been possible to achieve already for the tobacco system [[10]] Shillito, R. D. et al., Bto/Technology 3, (1985)].

2. Influence of the PEG concentration on the transformation rate

| PEG-concentration [%, w/v] | GPPL $\times 10^{-6}$ | ZT | RTF $\times 10^{-4}$ | ATF $\times 10^{-4}$ |
|---|---|---|---|---|
| PEG CMS4 | | *N. plumbaginifolia* | | |
| 8% | 0.72 | 2 | 0.13 | 0.03 (±0.02) |
| 13% | 1.05 | 7 | 0.26 | 0.063 (±0.035) |
| 20% | 0.90 | 22 | 1.45 | 0.25 (±0.06) |
| 24% | 1.0 | 32 | 2.0 | 0.32 (±0.07) |
| 27% | 1.0 | 46 | 3.1 | 0.46 (±0.05) |
| PEG CMS6 | | *N. Tabacum, SR₁* | | |
| 13% | 0.33 | 14 | — | 0.28 (±0.15) |
| 20% | 0.33 | 30 | — | 0.90 (±0.05) |
| 26 | 0.33 | 40 | — | 1.2 (±0.08) |

Table 2 shows clearly the influence of different PEG concentrations on the transformation frequencies that can be achieved with *N. tabacum* SR1 and *N. plumbaginifolia*. In both cases it is possible to distinguish a clear connection between the two parameters. On increasing the PEG concentration from 8% to 27% in the case of *N. plumbaginifolia* and from 13% to 26% in the case of *N. tabacum* SR1, the transformation frequencies achieved increase from $0.03 \times 10^{-4}$ to $0.28 \times 10^{-4}$ and from $0.46 \times 10^{-4}$ to $1.2 \times 10^{-4}$, respectively.

3. Influence of the MgCl₂ concentration on the transformation rate

TABLE 3

Influence of the MgCl₂ concentration, of the time of application, of the PEG solution used and, in the case of high PEG concentrations (>25%), of the washing conditions, on the transformation rate of *N. tabacum* SR1 protoplasts. PEG CMS4 and PEG CHS6 solutions with a final concentration of 20% are used for the transformation experiments (exceptions are indicated separately in the Table).

| Transformation | GPPL $\times 10^6$ | ZT | ATF $\times 10^{-3}$ |
|---|---|---|---|
| 1. controls | | | |
| W₅, no Mg²⁺ | 0.59 | 77 | 0.13 ± 0.03 |
| He Na/F, no Mg²⁺ | 0.26 | 265 | 1.0 ± 0.38 |
| MaMg 12mM, 8% PEG6R, 1500V, 3 Pulses, 1 KΩ, 10 nF | 0.26 | 324 | 1.3 ± 0.26 |
| MaMg 6mM, no PEG | 0.33 | 0 | |
| as above, +0.1M MgCl₂ after the addition of DNA | 0.33 | 0 | |
| 2. MgCl₂ addition directly before transformation | | | |
| W₅ + MaMg(1:1, MgCl₂ 4mM) | 0.37 | 1033 | 2.7 ± 0.46 |
| W₅ + MaMg(1:1, MgCl₂ 8mM) | 0.33 | 1087 | 3.3 ± 0.48 |
| MaMg 6mM | 0.50 | 2045 | 4.1 ± 0.51 |
| MaMg 12mM | 0.50 | 2056 | 4.1 ± 0.86 |
| 3. MgCl₂ addition 2 hours before transformation | | | |
| MaMg 6mM | 0.33 | 382 | 1.2 ± 0.30 |
| 4. PEG composition (MaMg 12mM) | | | |
| PEG CMS 4 (24%) | 0.32 | 693 | 2.2 ± 0.55 |
| PEG R6 (24%) | 0.32 | 474 | 1.5 ± 0.34 |
| 5. Washing conditions (MaMg 12mM; 25% PEG) | | | |
| CaCl₂.2H₂O 0.2M | 0.32 | 1127 | 3.5 ± 0.56 |
| W₅ | 0.32 | 686 | 2.1 ± 0.43 |

*MaMg...mM indicates the MgCl₂ concentration in a MaMg solution a) Time of application: As can be seen from Table 3, the best results, with a transformation rate of $4.1 \times 10^{-3}$, can be achieved by adding MgCl₂ to the transformation medium directly before the actual transformation.

If, on the other hand, the transformation is not carried out until hours after the MgCl₂ has been applied, the transformation rates are only $1.2 \times 10^{-3}$.

Also, combining a mannitol/MgCl₂ solution (MaMg solution) with a W₅ salt solution in a ratio of 1:1 results in a more or less pronounced decrease in the transformation frequency depending on the molar MgCl₂ concentration. If, for example, the MgCl₂ concentration of the MaMg solution is halved, this results in a decline in the transformation rate of approximately 20%.

On the other hand, comparing the results of the control experiments, which are carried out only in the presence of suitable buffer solutions (W5 solution or HeNa/F solution) [[39]]Fromm, M. et al., *Proc. Natl. Acad. Sci. USA* 85, 5842–5848, (1985)], but in the absence of Mg²⁺ ions, it can be seen that in those cases the transformation frequencies are lower by more than a power of ten. The high transformation rates discussed above cannot be achieved even using electroporation.

PEG/Mg$^{2+}$ synergism: The synergistic action in the case of simultaneous application of Mg$^{2+}$ ions and PEG is demonstrated very clearly in a comparison of the transformation results of the control tests that are carried out in the presence of MgCl$_2$ (6 mM) but without the addition of PEG, and also of the actual Examples in which MgCl$_2$ and PEG are used together (Tab. 3).

Control experiments in the presence of MgCl$_2$ in a concentration of 6 mM but without the addition of PEG do not result in any detectable incidents of transformation at all.

By contrast, the high transformation rates of 4.1×10$^-$ already mentioned above can be achieved by applying PEG (with a final concentration of 20%, w/v) into the MgCl-containing transformation medium directly after (from 0.1 to 10 minutes after) the addition of the DNA.

These transformation rates are thus also higher by more than a power of ten than the comparable results if using PEG alone without the addition of MgCla (cf. Tab. 2).

Figure 2:
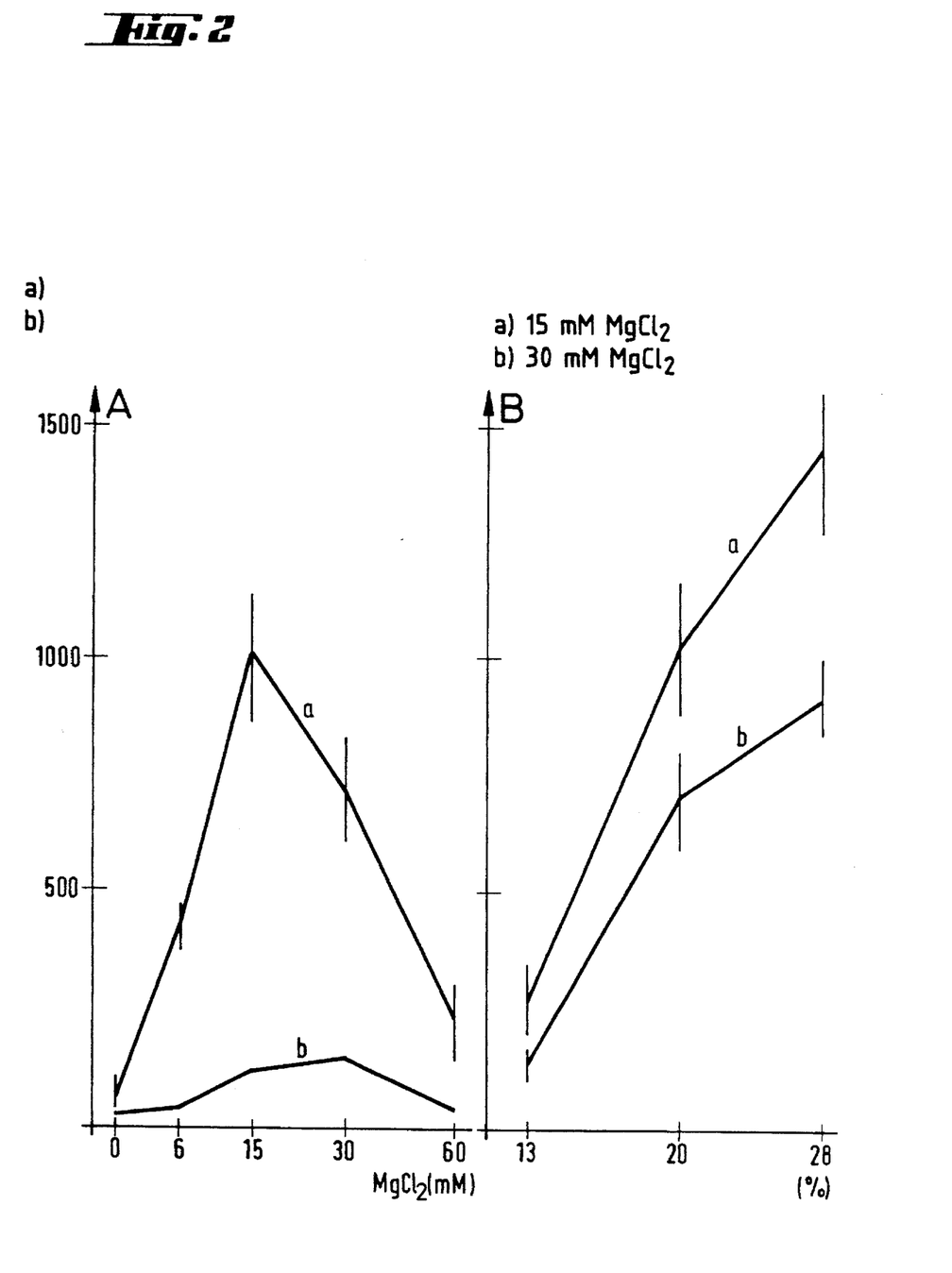
FIG. 2 demonstrates the influence of the MgCl$_2$ concentration (A) and of the MgCl$_2$/PEG interaction (B) on the transformation rates for *Nicotiana tabacum* c.v. Petit Havanna SR$_1$ (A and B) and for *Nicotiana plumbaginifolia* (A).

In contrast to tobacco, with which maximum transformation rates are achieved with a MgCl$_2$ concentration range of from 12 to 15 mM with, at the same time, a PEG CMS concentration of 28% (FIG. 2B), the optimum range in the case of *N. plumbaginifolia* tends towards higher MgCl$_2$ values (see FIG. 2A).

In that case, maximum transformation rates are achieved with MgCl$_2$ concentrations in a range of from 20 to 30 mM and with a PEG concentration of 20%. With these values, transformation rates of 3.9×10$^{-4}$ can be achieved.

PEG composition: Apart from the parameters already mentioned, the composition of the PEG solution used also has an effect on the transformation rates that can be achieved. Using PEG CMS [15] Negrutiu, I. et al., (1986a) and PEG 6R [10] Shillito, R. D. et al., (1985) under otherwise identical test conditions (PEG concentration 24%, MgCl$_2$ concentration 12 mM), in the former case distinctly higher transformation rates, which are higher by a factor of 1.4, can be achieved.

If high PEG concentrations of 24% (20% in the case of *N. plumbaginifolia*) are used, it has proved advantageous subsequently to wash the treated protoplasts with a 0.2M CaCl$_2$x2H$_2$O-containing solution.

As a result of that measure, the transformation rates can be increased by a factor of 1.7 compared with treatment with a simple salt solution (W$_5$ solution).

4. Detection of the transfer of the transformed gene to the sexual descendants and its hereditary transmission as a normal plant gene Extensive genetic hybridisation analyses and detailed molecular biological studies (for example Southern blot analysis of the DNA of the plant genome; examination of the enzyme activity of aminoglycosidephosphotransferase, that is to say the enzyme for kanamycin-specific phosphorylation) of the genetically modified plants (first generation and descendants) have produced the following results:

1. The bacterial gene is stably integrated into the plant genome;
2. As a rule, it is transferred unmodified and regularly to hybridisation descendants;
3. Its genotype corresponds to that of a natural, simple, dominant plant gene;
4. Molecular analysis by means of DNA hybridisation and enzyme test confirms the results of the genetic hybridisation analysis;
5. The genetically modified plants have retained their normal, natural phenotype during the treatment; thus, no undesired modifications have been ascertained.

These results show that the best method of controlled genetic modification of plant material has been found with the process of direct gene transfer into protoplasts according to the invention. The genetic modification is stable and undesired modifications of the genotype of the plant do not occur.

Literature:

1. Rothstein, S. J. and W. S. Reznikoff, *Cell*, 23, 191–199, (1981)
2. Herrera-Estrella, L. et al., *Nature*, 303, 209–213, (1983)
3. Bevan, M. W. and R. B. Flavell, *Nature*, 304, 184–187 (1983)
4. Chilton, M.-D., *Scientific American*, 248(6), 50–59 (1983)
5. Herrera-Estrella, L. et al., *EMBO J.*, 2(6), 987–995, (1983)
6. Murai, N. et al., *Science*, 222, 476–482 (1983)
7. Harsch, R. B. et al, *Science*, 223, 496–498 (1984)
8. Fraley, R. T. et al., *Proc. Natl. Acad. Sci. USA*, 80, 4803–4807 (1983)
9. Potrykus I. et al., *Plant Molec. Biol. Rep.*, 3 117–128, (1985)
10. Shillito, R. D. et al., *Bio/Technology*, 3, 1099–1103 (1985)
11. Neumann, E. et al., *EMBO J.*, 841–845 (1982)
12. Potrykus I. and Shillito, R. D., *Methods in Enzymology*, 118, 449–578 (1986), *Plant Molecular Biology*, eds. A & H. Weissbach, Academic Press, Orlando (1986)
13. Koblitz, H., Methodische Aspekte der Zell- und Gewebezüchtung bei Gramineen unter besonderer Berucksichtigung der Getreide Kulturpflanze XXII, 93–157 (1974)
14. McCutcheon's Detergents and Emulsifiers Annual, Mc Publishing Corp., Ridgewood New Jersey, 1981; Stache, H., "Tensid-Taschenbuch", Carl Hanser Verlag, Munnich/Vienna, 1981
15. Negrutiu, I. et al., *Theor. Appl. Genet.*, 72. 279–86 (1986a)
16. Wienand, U. et al., *Mol. Gen. Genet*, 182, 440–444 (1981)
17. Pennica, D. et al., *Nature*,.301, 214–221, (1983)
18. Stepien, P. et al., *Gene*, 24, 289–297, (1983)
19. Maniatis, T. et al., *Molecular Cloning*, Cold Spring Harbor Laboratory, 1982
20. Franck G. et al., *Cell*, 21: 285–294, 1980
21. Hohn et al., in: *"Molecular Biology of Plant Tumors"*, Academic Press, New York, page 549–560, 1982
22. Berry-Lowe et al., *J. Mol. Appl. Genet*, 1: 483–498, 1982
23. *Genetic Engineering of Plants, an Agricultural Perspective;* ed. A. Cashmore, Plenum, New York 1983, page 29–38
24. Coruzzi Get al.; *The Journal of Biological Chemistry*, 258: 1399, 1983
25. Dunsmuir P et al., *J. Mol. Appl. Genet.*, 2: 285, 1983
26. Gardner RC et al., *Nucl. Acids Res*, 9 (12): 2871–2888, 1981
27. Rodriguez, R. L. and Tait, R. C., *Recombinant DNA techniques*, Addison-Wesley Publishing Corp., London, Amsterdam, Don Mills, Ontario, Sydney, Tokyo, 1983
28. Messing, J. and Vieira, J., *Gene*, 19, 269–276, (1982)
29. Evans et al , "Protoplast Isolation and Culture" in *Handbook of Plant Cell Culture*, 1: 124–176 (Mac Millan Publishing Co., New York, 1983):
30. Davey MR, "Recent Developments in the Culture and Regeneration of Plant Protoplasts", *Protoplasts, 1983—Lecture Proceedings*, page 19–29, (Birkhäuser, Basel, 1983)

31. Dale PJ, "Protoplast Culture and Plant Regeneration of Cereals and other Recalcitrant Crops", in *Protoplasts 1983*—Lecture Proceedings, page 31–41 (Birkhäuser, Basel 1983)
32. Binding H "Regeneration of Plants", in *Plant Protoplasts* Seite 21–37, (CRC Press, Boca Raton, 1985).
33. Abdullah R et al., *Bio/Technology*, 4: 1087–1090, 1986
34. Fujimura T et al., *Plant Tissue Culture Lett.*, 2: 74–75, 1985
35. Toriyama K. et al., *Theor. Appl. Genet;* 73: 16–19, 1986
36. Yamada Y. et al., *Plant Cell Rep.* 5: 85–88, 1986
37. Southern, E. M., *J. Mol. Biol.*, 98, 503–517, (1975)
38. Rigby, W. J. et al., *J. Mol. Biol.*, 113, 237–251, (1977)
39. Fromm, M. et al., *Proc. Natl. Acad. Sci. USA*, 82, 5842–5848, (1985)
40. Shillito, R. D. et al., *Mutation Research*, 81, 165–175, (1981)
41. Nagy, J. I and P. Maliga, Z. Pflanzenphysiologie, 78, 453–455 (1976)
42. Installe, P. et al., *J. Plant Physiol.*, 119, 443–454, (1985)
43. Linsmaier, E. M. and Skook, F., *Physiol. Plant*, 18, 100–127, (1965)
44. Negrutiu, I. et al., *Theor. Appl. Genet.*, 66, 341–347 (1983)
45. Nitsch, J. P. and Nitsch C., *Science*, 163, 85–87, (1969)
46. Menczel, L. et al., *Theor. Appl. Genet*, 59, 191–195, (1981)
47. Beck, E. et al., *Gene*, 19, 327–336, (1982)
48. Jacobsen, H. et al., *Eur. J. Biochem.*, 45, 623, (1974)
49. Hohn B and Collins J., *Gene*, 11: 291–298, 1980
50. Soberon, X. et al., *Gene*, 9, 287–305, (1980)
51. Shillito, R. D. et al., *Plant Cell Reports*, 2, 244–247, (1983)

We claim:

1. A process for direct gene transfer into plant protoplasts that are amenable to transformation via direct gene transfer, which process consisting:

isolating plant protoplasts from plant tissue and culturing said protoplasts in a nutrient media customarily used for culturing plant protoplasts;

pre-incubating said protoplasts at a temperature of from 4° to 10° C. for from 20 minutes to 6 hours in a pre-incubation medium containing $Ca^{2+}$, $K^+$ and $Na^+$ ions and a suitable carbon source before the actual transformation;

separating said protoplasts from the pre-incubation medium and resuspending said protoplasts in a transformation medium which contains as an essential component from 6.0 to 60 mM $Mg^{2+}$ ions in the presence or absence of $Ca^{2+}$ ions;

directly thereafter, adding a DNA sample to said transformation medium;

from 0.1 to 10 minutes thereafter, adding polyethylene glycol (PEG) to said transformation medium; and incubating said protoplasts and DNA sample in said transformation medium for a period that is sufficient for the incorporation of said DNA into said protoplasts.

2. Process according to claim 1, wherein the pH value of the incubation solution is from pH 5.6 to pH 12.

3. Process according to claim 2, wherein the pH value of the incubation solution is from pH 7 to pH 10.

4. Process according to claim 1, wherein, in addition, neutral DNA without a transforming gene is added in excess as carrier DNA to the transformation solution.

5. Process according to claim 4, wherein the said neutral DNA is animal DNA, plant DNA, λ-DNA, plasmid DNA or any DNA suitable for carrying out the process.

6. Process according to claim 4, wherein the said neutral DNA is a calf's thymus carrier DNA.

7. Process according to claim 4, wherein the concentration of the carrier DNA is from 50 to 70 µg/ml.

8. Process according to claim 1, wherein the protoplasts and DNA are jointly incubated in said transformation medium, containing as an essential component from 6.0 to 60 mM $Mg^{2+}$ ions in the presence or absence of $Ca^{2+}$ ions, in the presence of polyethyleneglycol, for a period of from 10 minutes to 6 hours.

9. A process according to claim 1, wherein the protoplasts are from plants that can be regenerated from protoplasts.

10. Process according to claim 1, wherein the plant protoplasts used are those from a single species of plant or from a systematic unit subordinate to the species.

11. Process according to claim 10, wherein the said protoplasts are obtained from leaves, seedlings, stems, flowers, roots, pollen or embryos.

12. Process according to claim 11, wherein the protoplasts are leaf protoplasts.

13. Process according to claim 10, wherein the said protoplasts are obtained from cell cultures.

14. A process according to claim 1, wherein said DNA sample contains one or more genes under the control of expression signals active in plants which are capable of being expressed and replicated in plant cells and a supporting DNA.

15. Process according to claim 14, wherein the concentration of the DNA sample containing one or more genes of any origin under the control of expression signals that are active in plants, and a supporting DNA, is from 2 to 20 µg/ml.

16. Process according to claim 15, wherein the concentration of the said DNA sample is from 5 to 10 µg/ml.

17. Process according to claim 14, wherein the gene used is a gene of which the structural part is of plant, animal, microbial, viral or synthetic origin and of which the expression signals are of plant, animal or synthetic origin.

18. Process according to claim 17, wherein the transforming gene is composed of portions of more than one gene from the same organism.

19. Process according to claim 17, wherein the said transforming gene has a structural part that imparts a useful and desirable property to the plant being transformed.

20. Process according to claim 19, wherein the said structural gene imparts to the plant an increased resistance to, or tolerance of, pathogens, herbicides, insecticides and other biocides.

21. Process according to claim 19, wherein the said structural gene improves the formation and quality of reserve and stored substances in leaves, seeds, tubers, roots and stems.

22. Process according to claim 19, wherein the said structural gene codes for pharmaceutically acceptable active substances.

23. Process according to claim 17, wherein the said expression signals originate from genes of plants or plant viruses.

24. Process according to claim 17, wherein the transforming gene is composed of gene fragments from more than one strain, one variety or one species of the same organism.

25. Process according to claim 17, wherein the said transforming gene is composed both of genomic DNA, and of cDNA and/or synthetic DNA.

26. Process according to claim 17, wherein the transforming gene is composed of gene fragments from several organisms that belong to different genera.

27. Process according to claim 17, wherein the said transforming gene consists of genomic DNA, of a cDNA or of synthetic DNA.

28. Process according to claim 17, wherein the said expression signals originate from a plant gene that codes for the small subunit of ribulosebisphosphatecarboxylase or the chlorophyll a/b binding protein.

29. Process according to claim 17, wherein the said expression signals originate from genes of plant viruses.

30. Process according to claim 29, wherein the plant virus is Cauliflower Mosaic Virus (CaMV).

31. Process according to claim 29, wherein the expression signals are 35S expression signals of the CaMV genome.

32. Process according to claim 30, wherein the expression signals are the 19S expression signals of the CaMV genome.

33. A process for direct gene transfer into plant protoplasts that are amenable to transformation via direct gene transfer, which process comprising:

isolating plant protoplasts from plant tissue and culturing said protoplasts in a nutrient media customarily used for culturing plant protoplasts;

pre-incubating said protoplasts at a temperature of from 4° to 10° C. for from 20 minutes to 6 hours in a pre-incubation medium containing $Ca^{2+}$, $K^+$ and $Na^+$ ions and a suitable carbon source before the actual transformation;

separating said protoplasts from the pre-incubation medium and resuspending said protoplasts in a transformation medium which contains as an essential component from 10 to 30 mM $Mg^{2+}$ ions in the presence or absence of $Ca^{2+}$ ions;

directly thereafter, adding a DNA sample to said transformation medium;

from 0.1 to 10 minutes thereafter, adding polyethylene glycol (PEG) to said transformation medium; and incubating said protoplasts and DNA sample in said transformation medium for a period that is sufficient for the incorporation of said DNA into said protoplasts.

34. Process according to claim 33, wherein the final concentration of polyethylene glycol in the said incubation medium is from 10% to 30%.

\* \* \* \* \*